United States Patent
Andronic et al.

(10) Patent No.: US 9,796,274 B2
(45) Date of Patent: Oct. 24, 2017

(54) POWER DELIVERY SYSTEM FOR PROVIDING POWER TO SENSOR HEAD OF PAPER MACHINE OR OTHER SYSTEM

(71) Applicant: HONEYWELL ASCa, Inc., Mississauga (CA)

(72) Inventors: Cristian Andronic, Burnaby (CA); Michael J. Wardas, North Vancouver (CA); Jeffrey D. Austin, Maple Ridge (CA); Ronald E. Beselt, Burnaby (CA); Stuart James Heath, Surrey (CA); Bradley Humble, Vancouver (CA)

(73) Assignee: Honeywell Limited, Mississauga, Ontario (CA)

( * ) Notice: Subject to any disclaimer, the term of this patent is extended or adjusted under 35 U.S.C. 154(b) by 852 days.

(21) Appl. No.: 13/900,190

(22) Filed: May 22, 2013

(65) Prior Publication Data
US 2014/0345376 A1    Nov. 27, 2014

(51) Int. Cl.
*G01L 5/04* (2006.01)
*B60L 5/38* (2006.01)
(Continued)

(52) U.S. Cl.
CPC .............. *B60L 5/38* (2013.01); *G01N 33/346* (2013.01); *G01N 37/00* (2013.01); *G01N 2021/8663* (2013.01)

(58) Field of Classification Search
None
See application file for complete search history.

(56) References Cited

U.S. PATENT DOCUMENTS 3,296,710 A    1/1967  Krikorian
3,417,252 A    12/1968 Nickell et al.
(Continued)

FOREIGN PATENT DOCUMENTS

CA    2788122 A1    3/2013
CN    2022220309 A1    5/2012
FR    2660491 A1    10/1991

OTHER PUBLICATIONS

Tom Rosenberg, Product Line Manager, Balluff Inc., Understanding non-contact transmission of power and sensor signals, Design News, Jun. 1, 2001, www.designnews.com, 7 pages.
(Continued)

*Primary Examiner* — Peter Macchiarolo
*Assistant Examiner* — Jermaine Jenkins

(57) ABSTRACT

An apparatus includes a chassis configured to move back and forth along multiple rails. The apparatus also includes electrical contacts configured to form electrical connections to the rails. The apparatus further includes a power converter/conditioner configured to receive power from the rails via the electrical contacts and to convert the power into a different form and/or condition the power. In addition, the apparatus includes one or more sensors configured to measure at least one characteristic of a material, where the one or more sensors are configured to operate using the power from the power converter/conditioner. The electrical contacts could touch the rails and receive the power directly from the rails. The electrical contacts could also touch rail contacts and receive the power indirectly from the rails via the rail contacts.

21 Claims, 3 Drawing Sheets

(51) Int. Cl.
*G01N 37/00* (2006.01)
*G01N 33/34* (2006.01)
*G01N 21/86* (2006.01)

(56) References Cited

U.S. PATENT DOCUMENTS

| | | | |
|---|---|---|---|
| 3,552,203 | A | 1/1971 | Freeh |
| 3,574,261 | A | 4/1971 | Bailey |
| 3,879,607 | A | 4/1975 | Bjorklund |
| 3,886,371 | A | 5/1975 | Lloyd |
| 4,000,402 | A | 12/1976 | Higham |
| 4,134,781 | A | 1/1979 | Carstens et al. |
| 4,245,259 | A | 1/1981 | Pick |
| 4,271,699 | A | 6/1981 | Williamson |
| 4,314,868 | A | 2/1982 | Hirakawa et al. |
| 4,575,299 | A | 3/1986 | Layton et al. |
| 4,575,628 | A | 3/1986 | Bankart et al. |
| 4,733,078 | A | 3/1988 | Sturm |
| 4,879,471 | A * | 11/1989 | Dahlquist .................. 250/359.1 |
| 5,049,216 | A | 9/1991 | Shead et al. |
| 5,327,770 | A | 7/1994 | Hindle |
| 5,338,361 | A | 8/1994 | Anderson et al. |
| 5,663,565 | A | 9/1997 | Taylor |
| 5,773,714 | A * | 6/1998 | Shead ............................. 73/105 |
| 5,821,536 | A | 10/1998 | Pettit |
| 6,053,040 | A | 4/2000 | Callender et al. |
| 6,068,408 | A | 5/2000 | Mutoh et al. |
| 6,123,470 | A | 9/2000 | Chiu |
| 6,655,195 | B2 | 12/2003 | Grabscheid et al. |
| 6,743,337 | B1 | 6/2004 | Ischdonat |
| 6,813,542 | B2 | 11/2004 | Peshkin et al. |
| 6,832,864 | B2 | 12/2004 | Patton et al. |
| 6,895,811 | B2 | 5/2005 | Carey et al. |
| 6,907,317 | B2 | 6/2005 | Peshkin et al. |
| 7,120,508 | B2 | 10/2006 | Peshkin et al. |
| 7,148,499 | B2 | 12/2006 | Lapstun et al. |
| 7,235,890 | B1 | 6/2007 | Jasinski |
| 7,567,822 | B2 | 7/2009 | Hart et al. |
| 7,599,582 | B2 | 10/2009 | Beselt et al. |
| 7,678,233 | B2 | 3/2010 | Beselt |
| 7,819,034 | B2 * | 10/2010 | Jasinski ...................... 73/866.5 |
| 7,872,574 | B2 | 1/2011 | Betts et al. |
| 7,949,433 | B2 | 5/2011 | Hern et al. |
| 8,101,047 | B2 | 1/2012 | Kulma et al. |
| 8,104,363 | B2 | 1/2012 | Kinoshita |
| 8,219,025 | B2 * | 7/2012 | Andronic ................ H02J 17/00 340/10.34 |
| 8,229,486 | B2 * | 7/2012 | Hellstrom ............ G05B 19/042 455/39 |
| 8,561,468 | B2 | 10/2013 | Beselt et al. |
| 8,573,834 | B2 * | 11/2013 | Bik ................................ 374/10 |
| 8,979,258 | B2 * | 3/2015 | Usuda ........................ 347/102 |
| 9,004,638 | B2 * | 4/2015 | Wakayama et al. ............ 347/19 |
| 2002/0008167 | A1 | 1/2002 | Haberland et al. |
| 2002/0104637 | A1 | 8/2002 | Koivukunnas et al. |
| 2004/0182594 | A1 | 9/2004 | Chen et al. |
| 2004/0221978 | A1 | 11/2004 | Tran et al. |
| 2005/0192710 | A1 | 9/2005 | Thornton et al. |
| 2006/0243931 | A1 | 11/2006 | Haran et al. |
| 2006/0254367 | A1 | 11/2006 | Hellstrom |
| 2007/0039705 | A1 | 2/2007 | Stewart |
| 2007/0058212 | A1 | 3/2007 | Beselt et al. |
| 2008/0129495 | A1 | 6/2008 | Hitt |
| 2009/0073428 | A1 | 3/2009 | Magnus et al. |
| 2009/0099682 | A1 | 4/2009 | Jasinski |
| 2009/0229777 | A1 | 9/2009 | Tran et al. |
| 2009/0242157 | A1 | 10/2009 | Heintz et al. |
| 2009/0258604 | A1 | 10/2009 | Andronic |
| 2011/0284178 | A1 | 11/2011 | Shakespeare |
| 2011/0290438 | A1 | 12/2011 | Chu et al. |
| 2013/0055912 | A1 | 3/2013 | Beselt et al. |
| 2014/0320857 | A1 * | 10/2014 | Then et al. ................... 356/402 |
| 2014/0348154 | A1 * | 11/2014 | Hofman et al. .............. 370/350 |

OTHER PUBLICATIONS

Ronald E. Beselt, et al., "Scanning Sensor Arrangement for Paper Machines or Other Systems", U.S. Appl. No. 13/900,144, filed May 22, 2013.

International Search Report dated Jul. 30, 2014 in connection with International Patent Application No. PCT/CA2014/000412, 3 pages.

Written Opinon of International Searching Authority dated Jul. 30, 2014 2014 in connection with International Patent Application No. PCT/CA/2014/000412, 4 pages.

Final Office Action issued for U.S. Appl. No. 13/900,144, dated Dec. 16, 2015, 9 pgs.

Notice of Allowance issued for U.S. Appl. No. 13/900,144, dated Feb. 1, 2016, 6 pgs.

Office Action dated Jul. 16, 2015 in connection with U.S. Appl. No. 13/900,144, 15 pages.

European Patent Office, "Supplementary Partial European Search Report," Application No. 14800394.0-1559, Jan. 13, 2017, 8 pages, publisher EPO, Munich, Germany.

* cited by examiner

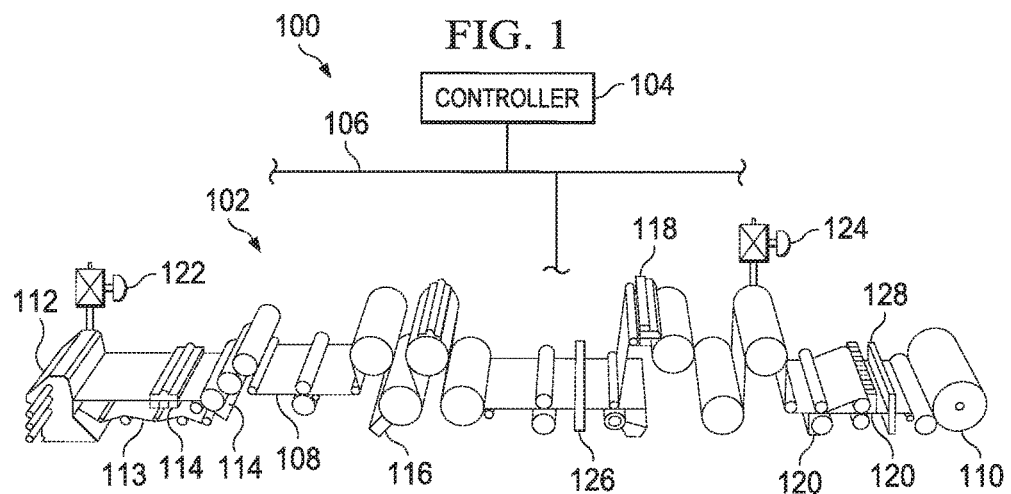
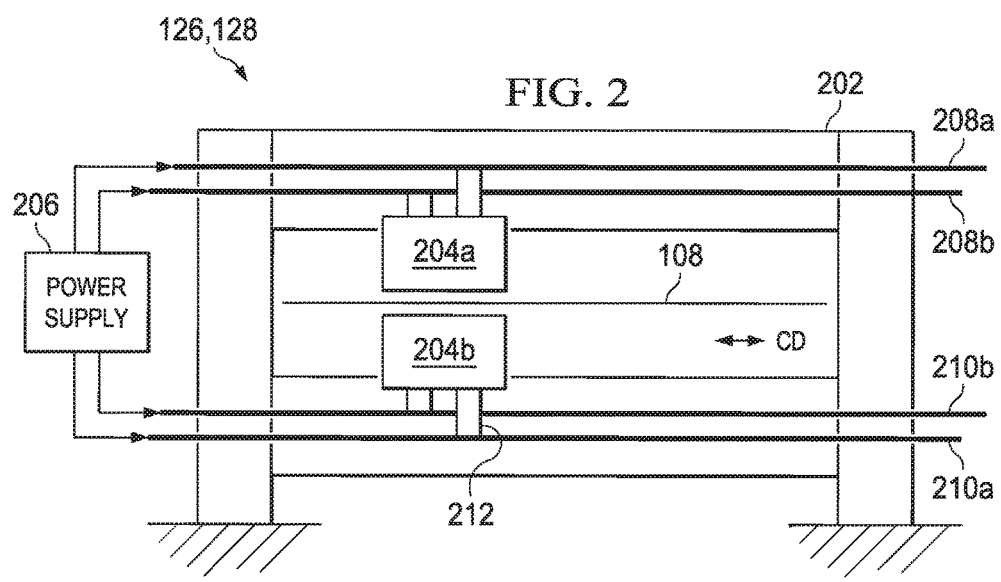

POWER DELIVERY SYSTEM FOR PROVIDING POWER TO SENSOR HEAD OF PAPER MACHINE OR OTHER SYSTEM

TECHNICAL FIELD

This disclosure relates generally to power delivery systems. More specifically, this disclosure relates to a power delivery system for providing power to a sensor head of a paper machine or other system.

BACKGROUND

Sheets or other webs of material are used in a variety of industries and in a variety of ways. These materials can include paper, multi-layer paperboard, and other products manufactured or processed in long webs. As a particular example, long sheets of paper can be manufactured and collected in reels.

It is often necessary or desirable to measure one or more properties of a web of material as the web is being manufactured or processed. Adjustments can then be made to the manufacturing or processing system to ensure that the properties stay within desired ranges. Measurements are often taken using one or more scanning sensor heads that move back and forth across the width of the web.

Electrical power is often carried to a scanning head through point-to-point wire connections. Since this cable structure moves with the scanning head, the cable structure typically has a folded arrangement, where an articulating linked exoskeleton allows electrical wires to be pushed and pulled back and forth with the moving scanning head.

SUMMARY

This disclosure describes a power delivery system for providing power to a sensor head of a paper machine or other system.

In a first embodiment, an apparatus includes a chassis configured to move back and forth along multiple rails. The apparatus also includes electrical contacts configured to form electrical connections to the rails. The apparatus further includes a power converter/conditioner configured to receive power from the rails via the electrical contacts and to convert the power into a different form and/or condition the power. In addition, the apparatus includes one or more sensors configured to measure at least one characteristic of a material, where the one or more sensors are configured to operate using the power from the power converter/conditioner.

In a second embodiment, a system includes a power supply configured to provide power over multiple rails and a sensor head. The sensor head includes a chassis configured to move back and forth along the rails. The sensor head also includes electrical contacts configured to form electrical connections to the rails. The sensor head further includes a power converter/conditioner configured to receive power from the rails via the electrical contacts and to convert the power into a different form and/or condition the power. In addition, the sensor head includes one or more sensors configured to measure at least one characteristic of a material, where the one or more sensors are configured to operate using the power from the power converter/conditioner.

In a third embodiment, a method includes moving a sensor head back and forth along multiple rails. The method also includes forming electrical connections to the rails at the sensor head. The method further includes receiving power from the rails via the electrical connections and converting the power into a different form and/or conditioning the power. In addition, the method includes measuring at least one characteristic of a material using one or more sensors of the sensor head, where the one or more sensors use the converted/conditioned power.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which:

FIG. 1 illustrates an example web manufacturing or processing system according to this disclosure;

FIG. 2 illustrates an example scanner that delivers power to scanning sensor heads according to this disclosure;

DETAILED DESCRIPTION

Figure 3:
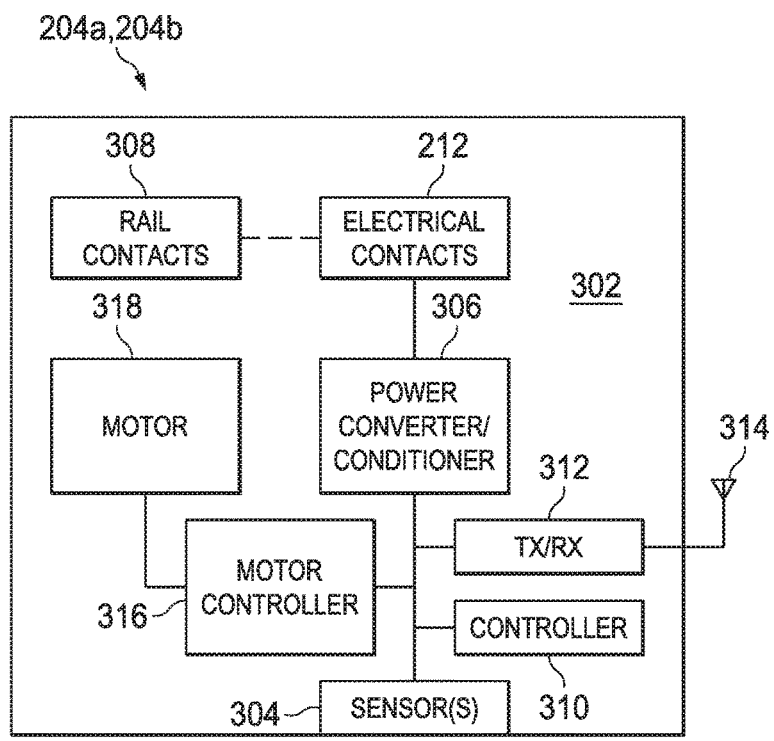
FIG. 3 illustrates additional details of an example scanning sensor head according to this disclosure.

FIGS. 1 through 5, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

FIG. 1 illustrates an example web manufacturing or processing system 100 according to this disclosure. In this example, the system 100 includes a paper machine 102, a controller 104, and a network 106. The paper machine 102 includes various components used to produce a paper product, namely a paper web 108 that is collected at a reel 110. The controller 104 monitors and controls the operation of the paper machine 102, which may help to maintain or increase the quality of the paper web 108 produced by the paper machine 102.

In this example, the paper machine 102 includes at least one headbox 112, which distributes a pulp suspension uniformly across the machine onto a continuous moving wire screen or mesh 113. The pulp suspension entering the headbox 112 may contain, for example, 0.2-3% wood fibers, fillers, and/or other materials, with the remainder of the suspension being water. The headbox 112 may include an array of dilution actuators, which distributes dilution water into the pulp suspension across the web. The dilution water may be used to help ensure that the resulting paper web 108 has a more uniform basis weight across the web 108.

Arrays of drainage elements 114, such as vacuum boxes, remove as much water as possible to initiate the formation of the web 108. An array of steam actuators 116 produces hot steam that penetrates the paper web 108 and releases the latent heat of the steam into the paper web 108, thereby increasing the temperature of the paper web 108 in sections across the web. The increase in temperature may allow for easier removal of remaining water from the paper web 108. An array of rewet shower actuators 118 adds small droplets of water (which may be air atomized) onto the surface of the paper web 108. The array of rewet shower actuators 118 may be used to control the moisture profile of the paper web 108, reduce or prevent over-drying of the paper web 108, or correct any dry streaks in the paper web 108.

The paper web 108 is then often passed through a calender having several nips of counter-rotating rolls. Arrays of induction heating actuators 120 heat the shell surfaces of various ones of these rolls. As each roll surface locally heats up, the roll diameter is locally expanded and hence increases nip pressure, which in turn locally compresses the paper web 108. The arrays of induction heating actuators 120 may therefore be used to control the caliper (thickness) profile of the paper web 108. The nips of a calender may also be equipped with other actuator arrays, such as arrays of air showers or steam showers, which may be used to control the gloss profile or smoothness profile of the paper web.

Two additional actuators 122-124 are shown in FIG. 1. A thick stock flow actuator 122 controls the consistency of incoming stock received at the headbox 112. A steam flow actuator 124 controls the amount of heat transferred to the paper web 108 from drying cylinders. The actuators 122-124 could, for example, represent valves controlling the flow of stock and steam, respectively. These actuators 122-124 may be used for controlling the dry weight and moisture of the paper web 108.

Additional components could be used to further process the paper web 108, such as a supercalender (for improving the paper web's thickness, smoothness, and gloss) or one or more coating stations (each applying a layer of coatant to a surface of the paper to improve the smoothness and printability of the paper web). Similarly, additional flow actuators may be used to control the proportions of different types of pulp and filler material in the thick stock and to control the amounts of various additives (such as retention aid or dyes) that are mixed into the stock.

This represents a brief description of one type of paper machine 102 that may be used to produce a paper product. Additional details regarding this type of paper machine 102 are well-known in the art and are not needed for an understanding of this disclosure. Also, this represents one specific type of paper machine 102 that may be used in the system 100. Other machines or devices could be used that include any other or additional components for producing a paper product. In addition, the control system described below is not limited to use with systems for producing paper products and could be used with systems that process a paper product or with systems that produce or process other items or materials (such as multi-layer paperboard, cardboard, plastic, textiles, metal webs, or other or additional materials that are manufactured or processed as moving webs).

In order to control the paper-making process, one or more properties of the paper web 108 may be continuously or repeatedly measured. The web properties can be measured at one or various stages in the manufacturing process. This information may then be used to adjust the paper machine 102, such as by adjusting various actuators within the paper machine 102. This may help to compensate for any variations of the web properties from desired targets, which may help to ensure the quality of the web 108.

As shown in FIG. 1, the paper machine 102 includes one or more scanners 126-128, each of which may include one or more sensors. Each scanner 126-128 is capable of measuring one or more characteristics of the paper web 108. For example, each scanner 126-128 could include sensors for measuring the caliper, anisotropy, basis weight, color, gloss, sheen, haze, surface features (such as roughness, topography, or orientation distributions of surface features), or any other or additional characteristics of the paper web 108.

Each scanner 126-128 includes any suitable structure or structures for measuring or detecting one or more characteristics of the paper web 108. For example, each scanner 126-128 could include one or more sets of sensors mounted on a scanning head that moves back and forth across the web 108. Note, however, that stationary sensors could also be used at one or more locations of the paper machine 102.

The controller 104 receives measurement data from the scanners 126-128 and uses the data to control the paper machine 102. For example, the controller 104 may use the measurement data to adjust any of the actuators or other components of the paper machine 102. The controller 104 includes any suitable structure for controlling the operation of at least part of the paper machine 102, such as a computing device.

The network 106 is coupled to the controller 104 and various components of the paper machine 102 (such as the actuators and scanners). The network 106 facilitates communication between components of the system 100. The network 106 represents any suitable network or combination of networks facilitating communication between components in the system 100. The network 106 could, for example, represent a wired or wireless Ethernet network, an electrical signal network (such as a HART or FOUNDATION FIELDBUS network), a pneumatic control signal network, or any other or additional network(s).

In general, at least one of the scanners 126-128 includes a scanning sensor head that moves back and forth across a surface of the web 108. Each scanning sensor head typically moves across the width of the web 108 in the "cross direction" (CD). There may be a single sensor head that moves across the entire width of the web 108, or multiple sensor heads may each move across a part of the width of the web 108. There could also be one or more sensor heads located on each side of the web 108. As noted above, electrical power is often provided to scanning sensor heads through cables that form point-to-point wire connections. Articulating linked exoskeletons are used to allow the cables to be pushed and pulled back and forth with the moving scanning heads.

Unfortunately, scanning sensor heads often travel back and forth hundreds of thousands or even millions of times during their operational lifespans. Due to the large number of times that the cable assemblies are pushed and pulled, the development and testing of cable structures, supports, carrier linkages, and end terminations are typically expensive. Moreover, expensive construction materials such as polytetrafluoroethylene (PTFE), high-purity fine-strand wires, and interface layers are often needed to achieve adequate operational lifespans for the cable assemblies.

Ultimately, each cable assembly is a moving system and has a limited lifetime, which necessitates costly replacement of cable assemblies on a periodic or other basis. Moreover, failures of cable assemblies can occur unexpectedly, and unplanned machine shutdowns for repairs add to the cost of using the cable assemblies. Beyond that, an articulating cable assembly typically folds on itself and requires a significant amount of space to ensure that wires are not flexed too sharply, and the space that holds a cable assembly often needs to include an access opening along the entire length of the scanner. Sometimes, the access openings need to be sealed, which adds additional cost, complexity, and failure points to the system. Other times, the access openings can remain open, but this allows process debris to become trapped. This can cause additional wear on the system and is particularly problematic in applications with critical cleanliness specifications.

As described in more detail below, these and other problems can be reduced or eliminated using a scanning sensor head that receives operating power from multiple rails. This can reduce the number of cables that need to be connected to the scanning sensor head. Additional features, such as the use of a wireless radio to transmit sensor measurements, can be used to completely eliminate cables connected to the scanning sensor head. Reducing or eliminating the use of cables that are pushed and pulled with a sensor head can greatly simplify installation and maintenance and reduce operational costs and failure rates.

Although FIG. 1 illustrates one example of a web manufacturing or processing system 100, various changes may be made to FIG. 1. For example, other systems could be used to produce other paper or non-paper products. Also, while shown as including a single paper machine 102 with various components and a single controller 104, the system 100 could include any number of paper machines or other machinery having any suitable structure, and the system 100 could include any number of controllers. In addition, FIG. 1 illustrates one operational environment in which power can be provided to a scanning sensor head. This functionality could be used in any other type of system, and that system need not manufacture or process moving webs or webs.

FIG. 2 illustrates an example scanner 126, 128 that delivers power to scanning sensor heads according to this disclosure. As shown in FIG. 2, the scanner includes a frame 202, which represents a structure that defines a space in which a web 108 can pass. The space within the frame 202 also includes various other components of the scanner. The frame 202 can be formed from any suitable material(s), such as metal. The frame 202 can also be formed in any suitable manner, such as welding. In addition, while shown here as being secured to the ground, the frame 202 could be secured to any other suitable structure.

The scanner here also includes multiple sensor heads 204a-204b. Each sensor head 204a-204b generally includes one or more sensors capable of measuring at least one characteristic of the web 108. For example, each sensor head 204a-204b could include sensors for measuring the moisture, caliper, anisotropy, basis weight, color, gloss, sheen, haze, surface features (such as roughness, topography, or orientation distributions of surface features), or any other or additional characteristics of the web 108. Each sensor head 204a-204b includes any suitable structure or structures for measuring or detecting one or more characteristics of a web.

In this example, at least one power supply 206 provides operating power to the sensor head 204a-204b. Each power supply 206 represents any suitable source of operating power for one or more sensor heads. A power supply 206 could, for example, represent at least one AC and/or DC voltage source(s). Power supplies with lower voltage levels can be used to comply with low-voltage directives for safety, or power supplies with higher voltage levels can be used to support lower current levels and less arcing damage through electrical contacts. In particular embodiments, the power supply 206 represents an AC power supply with an expected range of 20-40 VAC at 50-60 Hz.

Power from the power supply 206 is provided to the sensor heads 204a-204b via multiple sets of rails. In this example, two rails 208a-208b electrically couple the sensor head 204a to the power supply 206. Similarly, two rails 210a-210b electrically couple the sensor head 204b to the power supply 206. Moreover, each set of rails 208a-208b and 210a-210b could also be used to support the corresponding sensor head 204a-204b, respectively. In other words, the sensor head 204a could actually ride on the rails 208a-208b and need no other external support, and the sensor head 204b could actually ride on the rails 210a-210b and need no other external support. Note, however, that a separate support structure on which a sensor head rides could also be used in conjunction with rails for providing power to the sensor head. Each of the rails 208a-208b, 210a-210b represents any suitable conductive structure that can be used to supply power to a sensor head.

In this example, there are two rails 208a-208b or 210a-210b used to supply power to each sensor head 204a or 204b. In this embodiment, one rail 208a, 210a could be used as a voltage supply rail (DC) or as a voltage line #1 (AC), and the other rail 208b, 210b could be used as a voltage return rail (DC) or as a voltage line #2 (AC). However, more than two rails can be used to power each sensor head. For example, additional rails can be used to provide alternate voltage levels or types or to provide redundancy in the scanner.

Each sensor head 204a-204b here includes electrical contacts 212 for receiving operating power from its respective rails 208a-208b, 210a-210b. Any suitable electrical contacts 212 can be used in a sensor head to receive operating power from two or more rails. In some embodiments, the electrical contacts 212 represent brushes, rollers, sliders, or other structures used to form electrical connections directly on the rails. In other embodiments, the electrical contacts 212 represent brushes, rollers, sliders, or other structures used against rail contacts that contact the rails (such as bearing assemblies or wheels), thereby providing indirect electrical connections with the rails. Each electrical contact 212 includes any suitable structure for forming a direct or indirect electrical connection to a rail.

Note that various additional features could be used in the scanner of FIG. 2. For example, each rail could be partially covered by a U-shaped enclosure that is partially opened along at least one side, which allows an electrical contact and/or a rail contact to physically contact the rail. The enclosure can be formed from insulative material(s) so that an electrical connection to the rail cannot be formed except along the opening of the enclosure. Spacers within the enclosure can contact the rail and help to maintain the position of the enclosure on the rail. Any suitable number and type of spacers could be used.

Also, while the two rails 208a-208b or 210a-210b are shown here as being spaced apart, this is not required. For instance, the rails 208a-208b or 210a-210b could form part of a single rail case having an external conductive shell with at least one opening exposing an inner conductor. In this arrangement, the outer conductive shell could represent one rail, and the inner conductor could represent the other rail. Brushes or other electrical contacts 212 could contact the outer conductive shell and the inner conductor through the opening(s) in the outer shell. Any other suitable arrangement for the rails could be used.

Although FIG. 2 illustrates one example of a scanner 126, 128 that delivers power to scanning sensor heads, various changes may be made to FIG. 2. For example, a scanner could include a single sensor head on one side of the web 108.

FIG. 3 illustrates additional details of an example scanning sensor head 204a, 204b according to this disclosure. As shown in FIG. 3, the sensor head 204a, 204b includes a moveable chassis 302, which represents a housing or other structure configured to encase, contain, or otherwise support other components of the sensor head 204a, 204b. The chassis 302 can be formed from any suitable material(s) (such as metal) and in any suitable manner.

The sensor head 204a, 204b also includes one or more sensors 304 that capture measurements associated with the web 108 or other material(s). Each sensor 304 includes any suitable structure for capturing measurements associated with one or more characteristics of a web. A sensor 304 could represent a contact sensor that takes measurements of a web via contact with the web or a non-contact sensor that takes measurements of a web without contacting the web. Each sensor head 204a, 204b could include any number of sensors 304.

The sensor head 204a, 204b further includes a power converter/conditioner 306. The power converter/conditioner 306 is electrically connected to two or more rails 208a-208b, 210a-210b and receives electrical power from the rails. As described above, electrical contacts 212 may be used to contact the rails 208a-208b directly or indirectly, such as via rail contacts 308. The power converter/conditioner 306 can receive electrical power and convert the electrical power into a form suitable for use in a sensor head. For example, the power converter/conditioner 306 could receive AC power from the power supply 206 and convert the AC power into a DC form, or the power converter/conditioner 306 could receive DC power from the power supply 206 and convert the DC power into a different DC form. As a particular example, the power converter/conditioner 306 could receive a 20-40 VAC 50 Hz signal from the power supply 206 and convert the signal into a 24 VDC signal. The power converter/conditioner 306 could also condition the received power, such as by filtering the received power (with or without also converting the form of the power). The power converter/conditioner 306 includes any suitable structure for converting power from one form to another and/or conditioning power.

The rail contacts 308 couple the sensor head 204a, 204b to the rails 208a-208b, 210a-210b so that the sensor head can move back and forth on the rails. The rail contacts 308 can also optionally be used to provide power from the rails to the electrical contacts 212. For example, the rail contacts 308 can allow electrical currents to flow between the rails and the power converter/conditioner 306. Each rail contact 308 includes any suitable structure(s) for coupling a sensor head to a rail. In some embodiments, each rail contact 308 includes a bearing assembly, a bearing wheel, or a slider.

A controller 310 controls the overall operation of the sensor head 204a, 204b. For example, the controller 310 could receive measurements from one or more sensors 304 and control wireless transmission of the sensor measurements to one or more destinations. The controller 310 includes any suitable processing or control device(s), such as one or more microprocessors, microcontrollers, digital signal processors, field programmable gate arrays, or application specific integrated circuits. Note that the controller 310 could also be implemented as multiple devices.

A wireless transceiver 312 is coupled to one or more antennas 314. The wireless transceiver 312 facilitates the wireless transmission and reception of data, such as by transmitting sensor measurements and related data to a control system and receiving commands from the control system. The wireless transceiver 312 includes any suitable structure for generating signals for wireless transmission and/or for processing signals received wirelessly. In particular embodiments, the wireless transceiver 312 represents a radio frequency (RF) transceiver. Note that the transceiver 312 could be implemented using a transmitter and a separate receiver. The antenna 314 represents any suitable structure for transmitting and receiving wireless signals, such as an RF antenna.

A motor controller 316 can be used to control the operation of a motor 318 in the sensor head 204a, 204b. The motor 318 can be used to move the sensor head 204a, 204b back and forth along the rails 208a-208b, 210a-210b. The motor controller 316 could generate and output pulse width modulation (PWM) or other control signals for adjusting the direction and speed of the motor 318. The direction and speed could be controlled based on input from the controller 310. The motor controller 316 includes any suitable structure for controlling the operation of a motor. Note, however, that the sensor head 204a, 204b could be moved in other ways and need not include a motor and motor controller. For instance, an external motor could rotate a belt coupled to the sensor head 204a, 204b.

Although FIG. 3 illustrates additional details of one example of a scanning sensor head 204a, 204, various changes may be made to FIG. 3. For example, various components in FIG. 3 could be combined, further subdivided, or omitted and additional components could be added according to particular needs.

Figure 4A:
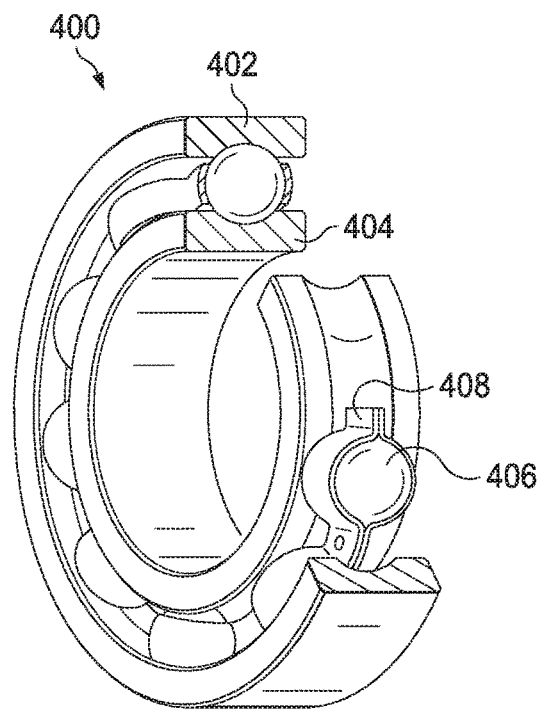
FIGS. 4A and 4B illustrate example rail contacts through which power can be delivered to a scanning sensor head according to this disclosure.
Figure 4B:
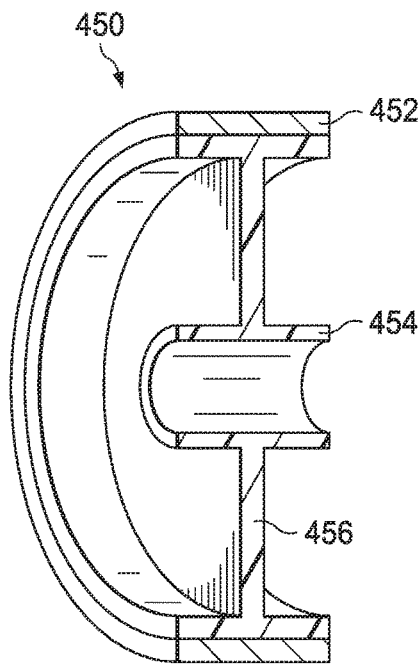

FIGS. 4A and 4B illustrate example rail contacts through which power can be delivered to a scanning sensor head according to this disclosure. In particular, FIG. 4A illustrates an example bearing assembly 400, and FIG. 4B illustrates an example bearing wheel 450. The bearing assembly 400 or bearing wheel 450 could, for example, form at least a portion of a rail contact 308 in the sensor head 204a, 204b.

As shown in FIG. 4A, the bearing assembly 400 includes an outer race 402, an inner race 404, bearings 406, and a cage 408. The outer race 402 and the inner race 404 generally form a channel in which the bearings 406 and cage 408 reside. The inner race 404 can rotate independent of the outer race 402. The bearings 406 help to facilitate this rotation by rolling within the channel between the outer and inner races 402-404. The cage 408 helps to maintain the separation of the bearings 406.

Each of the outer and inner races 402-404 includes any suitable structure along which bearings can roll. Each bearing 406 includes any suitable structure that can roll between two races. The cage 408 includes any suitable structure for maintaining separation of multiple bearings.

This represents one example way in which a bearing assembly can be formed. Many alternate designs exist for a bearing assembly. For example, while shown as having spherical bearings 406, the bearings 406 could have other shapes, such as cylindrical forms. Also, a cage 408 can be implemented in numerous other ways.

As noted above, the electrical contacts 212 could contact the rails 208a-208b, 210a-210b directly or indirectly. Indirect connection to the rails could be made via the rail contacts 308. As an example of the indirect path, current can travel from one rail through the bearing assembly 400 to the power converter/conditioner 306. The current can then return to another rail via another bearing assembly 400.

A current flowing through the bearing assembly 400 could follow any suitable current path. For example, the outer race 402 could contact both a rail and an electrical contact 212, such as a brush or roller. In this case, current could flow through the outer race 402, and the bearings 406 could be insulated so that no current flows through the bearings 406. As another example, the outer race 402 could contact a rail, and an electrical contact 212 could contact the inner race 404. In that case, current could flow through the outer race 402 and the bearings 406 to the inner race 404 (or in the opposite direction).

In FIG. 4B, the bearing wheel 450 includes an outer race 452, an inner race 454, and a connector 456 that fixedly connects the outer and inner races 452-454. Current passing through the bearing wheel 450 between a rail and an electrical contact 212 could pass through the outer racer 452 only, through the outer race 452 and the connector 456, or through all three components 452-456 of the bearing wheel 450. If current does not pass through the inner race 454 or the connector 456, one or both of these components 454-456 could be formed from any suitable insulative material(s).

These represent example ways in which power can be provided to a sensor head via two rails. Various other rail contacts 308 could also be used, such as sliders made of carbon, graphite, or other suitable material(s) that simply slide along the rails. Also, as noted above, power for a sensor head may or may not be received through a rail contact.

Although FIGS. 4A and 4B illustrate examples of rail contacts through which power can be delivered to a scanning sensor head, various changes may be made to FIGS. 4A and 4B. For example, as noted above, various types of bearing assemblies or other rail contacts can be used.

Figure 5:
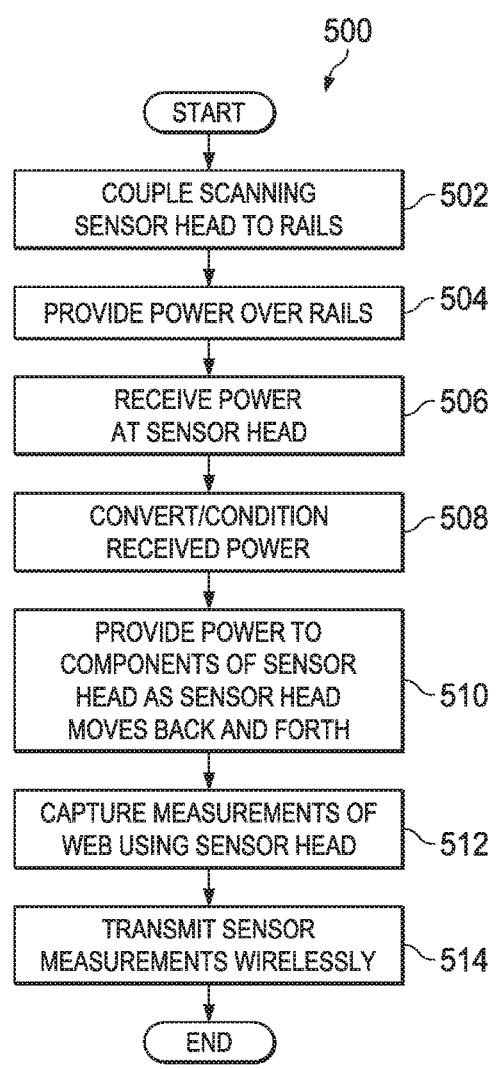
FIG. 5 illustrates an example method for power delivery to a scanning sensor head according to this disclosure.

FIG. 5 illustrates an example method 500 for power delivery to a scanning sensor head according to this disclosure. As shown in FIG. 5, a scanning sensor head is coupled to multiple rails at step 502. This could include, for example, mounting a sensor head 204a, 204b on two or more rails 208a-208b, 210a-210b of a scanner.

Power is provided over the rails at step 504. This could include, for example, the power supply 206 supplying AC or DC power over the rails 208a-208b, 210a-210b. The power is received at the sensor head at step 506 and converted/conditioned at step 508. This could include, for example, the power converter/conditioner 306 receiving the power from the rails 208a-208b, 210a-210b directly via the electrical contacts 212 or indirectly, such as via the rail contacts 308. This could also include the power converter/conditioner 306 converting AC or DC power into a suitable DC form or otherwise converting the form of the received power. This could further include the power converter/conditioner 306 conditioning the received power (with or without converting the form of the power).

Power is provided to components of the sensor head as the sensor head moves back and forth at step 510. This could include, for example, the power converter/conditioner 306 providing operating power to the sensor(s) 304, controller 310, and transceiver 312 of the sensor head. This could also include the power converter/conditioner 306 providing operating power to the motor controller 316 and the motor 318. Using this power, sensor measurements of a web are captured at step 512 and wirelessly transmitted at step 514. This could include, for example, the sensor(s) 304 providing sensor measurements directly to the transceiver 312 for transmission or to the controller 310 for processing before transmission.

Although FIG. 5 illustrates one example of a method 500 for power delivery to a scanning sensor head, various changes may be made to FIG. 5. For example, FIG. 5 assumes that a sensor head in the paper machine 102 is being powered through the rails. However, the same general steps can be used to power any other suitable device, such as any other sensor device that can move on or along one or more rails. Also, while shown as a series of steps, various steps in FIG. 5 could overlap, occur in parallel, occur in a different order, or occur any number of times.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
   a chassis configured to move back and forth along multiple rails;
   rail contacts configured to touch the rails, wherein each rail contact comprises an outer race and an inner race;
   electrical contacts configured to touch the rail contacts to form electrical connections to the rails and receive power from the rails via the rail contacts;
   a power converter/conditioner configured to receive the power from the rails via the electrical contacts and to at least one of: convert the power into a different form and condition the power; and
   one or more sensors configured to measure at least one characteristic of a material, the one or more sensors configured to operate using the power from the power converter/conditioner.

2. The apparatus of claim 1, wherein the electrical contacts touch one of the inner races and the outer races of the rail contacts to receive the power from the rails.

3. The apparatus of claim 1, wherein:
   the outer race of each rail contact is configured to contact (i) one of the rails and (ii) one of the electrical contacts; and
   bearings located between the outer and inner races of each rail contact are insulative.

4. The apparatus of claim 1, wherein:
   the outer race of each rail contact is configured to contact one of the rails; and
   the inner race of each rail contact is configured to contact one of the electrical contacts.

5. The apparatus of claim 1, wherein each rail contact further comprises a connector fixedly connecting the outer and inner races of that rail contact.

6. The apparatus of claim 5, wherein each rail contact is configured to pass electrical current through the outer race and the connector of that rail contact.

7. The apparatus of claim 1, wherein the electrical contacts are configured to touch the rail contacts to form the electrical connections such that current paths between the rails and the electrical contacts pass through at least the outer races of the rail contacts.

8. The apparatus of claim 1, further comprising:
a wireless transceiver configured to wirelessly transmit sensor measurements from the one or more sensors.

9. The apparatus of claim 1, further comprising:
a motor configured to move the chassis back and forth along the rails; and
a motor controller configured to control the motor.

10. The apparatus of claim 1, wherein the chassis is configured to move back and forth on the rails.

11. The apparatus of claim 1, wherein:
the chassis is configured to move back and forth on the rails; and
the electrical contacts are located on or in the chassis.

12. A system comprising:
a power supply configured to provide power over multiple rails; and
a sensor head comprising:
  a chassis configured to move back and forth along the rails;
  rail contacts configured to touch the rails, wherein each rail contact comprises an outer race and an inner race;
  electrical contacts configured to touch the rail contacts to form electrical connections to the rails and receive power from the rails via the rail contacts;
  a power converter/conditioner configured to receive the power from the rails via the electrical contacts and to at least one of: convert the power into a different form and condition the power; and
  one or more sensors configured to measure at least one characteristic of a material, the one or more sensors configured to operate using the power from the power converter/conditioner.

13. The system of claim 12, wherein:
the power supply is configured to provide the power over multiple sets of rails; and
the system includes multiple sensor heads configured to receive the power via different sets of rails.

14. The system of claim 13, wherein the sensor heads are configured to measure the at least one characteristic of a web of the material on opposite sides of the web.

15. The system of claim 12, wherein:
the outer race of each rail contact is configured to contact (i) one of the rails and (ii) one of the electrical contacts; and
bearings located between the outer and inner races of each rail contact are insulative.

16. The system of claim 12, wherein:
the outer race of each rail contact is configured to contact one of the rails; and
the inner race of each rail contact is configured to contact one of the electrical contacts.

17. The system of claim 12, wherein each rail contact further comprises a connector fixedly connecting the outer and inner races of that rail contact.

18. The system of claim 17, wherein at least one of the connector and the inner race of each rail contact is insulative.

19. The system of claim 12, wherein the sensor head further comprises a wireless transceiver configured to wirelessly transmit sensor measurements from the one or more sensors.

20. A method comprising:
moving a sensor head back and forth along multiple rails;
forming electrical connections to the rails at the sensor head using rail contacts that touch the rails and electrical contacts that touch the rail contacts;
receiving power from the rails via the electrical connections and at least one of: converting the power into a different form and conditioning the power; and
measuring at least one characteristic of a material using one or more sensors of the sensor head, the one or more sensors using the converted/conditioned power;
wherein the electrical contacts receive the power from the rails via the rail contacts; and
wherein each rail contact comprises an outer race and an inner race.

21. The method of claim 20, wherein current paths between the rails and the electrical contacts pass through at least the outer races of the rail contacts.

* * * * *